United States Patent
Zhang

(10) Patent No.: US 7,741,342 B2
(45) Date of Patent: Jun. 22, 2010

(54) WATER-SOLUBLE THALIDOMINE DERIVATIVES

(75) Inventor: Hesheng Zhang, No. 79, Duolun Street, Heping District, Tianjin City, 300020 (CN)

(73) Assignees: Hesheng Zhang, Tianjin (CN); Fengsheng Che, Hainan (CN)

( * ) Notice: Subject to any disclaimer, the term of this patent is extended or adjusted under 35 U.S.C. 154(b) by 1072 days.

(21) Appl. No.: 10/547,054

(22) PCT Filed: Mar. 4, 2004

(86) PCT No.: PCT/CN2004/000167

§ 371 (c)(1),
(2), (4) Date: Aug. 24, 2005

(87) PCT Pub. No.: WO2004/085422

PCT Pub. Date: Oct. 7, 2004

(65) Prior Publication Data

US 2006/0094730 A1    May 4, 2006

(30) Foreign Application Priority Data

Mar. 27, 2003    (CN) ................... 03 1 20994

(51) Int. Cl.
*A61K 31/4545* (2006.01)
*C07D 403/14* (2006.01)

(52) U.S. Cl. .................. 514/323; 514/256; 514/318; 544/333; 546/194; 546/200

(58) Field of Classification Search ................ 514/256, 514/318, 323; 544/333; 546/194, 200
See application file for complete search history.

(56) References Cited

U.S. PATENT DOCUMENTS

2008/0051432 A1* 2/2008 Zhang .................... 514/323

OTHER PUBLICATIONS

Schneider et al. "Acylated N-hydroxymethylthalidomide . . ." CA 127:331403 (1997).*
"Derivative" Dictionary (2009) (from internet).*
Bundgaard "Design of prodrugs" p. 8 (1985).*
Zhang et al. "Preparation of water . . ." CA 141:295871 (2004).*
Wadler "Thalidomide for advaced . . ." Am. Cancer Soc. v.103(1)p. 1-4 (2004).*

\* cited by examiner

*Primary Examiner*—Celia Chang
(74) *Attorney, Agent, or Firm*—Matthias Scholl P.C.; Matthias Scholl

(57) ABSTRACT

Thalidomide derivative (I) and their bases or salts are new: where R represents $CHR^1NR^2R^3$, $CHR^1NR^4C(O)CHR^5NR^2R^3$, W or $CHR^5NR^4C(O)W$, where $R^1$, $R^4$ and $R^5$ represent independently each other H, $C_{1-4}$ alkyl, $R^2$ is a $C_{1-4}$ alkyl, $R^3$ is a $C_{1-4}$ alkyl, or $R^2$ and $R^3$ together represents 1,3-propylene, 1,4-butylene, 1,5-pentylene, 1,6-hexylene, W represents 4-, 5-, 6-, 7-, or 8-mumbered, saturated or unsaturated heterocycle. The invention also relates to processes of production thereof and the use of thereof as an active pharmaceutical ingredient.

(I)

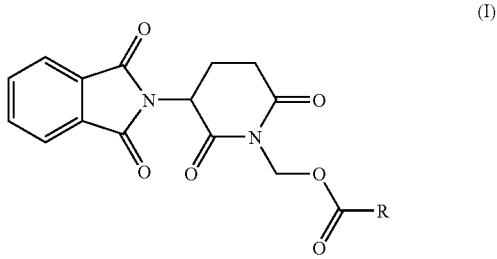

5 Claims, No Drawings

WATER-SOLUBLE THALIDOMINE DERIVATIVES

BACKGROUND OF THE PRESENT INVENTION

1. Field of Invention

The present invention relates to thalidomide derivatives, the method of producing thereof, and the application thereof as an active pharmaceutical ingredient.

2. Description of Related Arts

In 1953, thalidomide was synthesized and extensively used as a depressant and preventive medicine for vomiting in pregnant women. In the early 1960s, the serious reproductive toxicity had been identified. However, some of the properties of thalidomide, such as the inhibition in the releasing of Tumor Necrosis Factor-α (TNF$_\alpha$), anti-angiogenesis and anti-inflammatory characteristics, make it more effective in the treatment of erythema nodosum leprosum (ENL), cutaneous erythematosus lupes (Arch. Dermatol, 1993, Vol. 129 P. 1548-1550), persistent erythematosus lupes (The Journal of Rheumatology, 1989, 16, P. 923-92), Behcet's syndrome (Arch. Dermatol. 1990, vol. 26, P. 923-927), Crohn's disease (Journal of Pediatr. Gastroenerol. Nurt. 1999, vol. 28, P. 214-216) and rheumatoid arthritis (Journal of Rheumatology, 1988, vol. 25, P. 264-969). Furthermore, thalidomide has been extensively used in clinical trials for the treatment of malignant tumors when these tumors show strong angiogenesis and chemotherapy refractory. In 1998, the FDA of the United States approved the use of thalidomide for treating ENL. In addition, the reproductive toxicity of thalidomide has been completely controlled by birth-control, especially in those patients who are in critical condition. However, since thalidomide is only slightly soluble in water (0.012 mg/mL, Arch. Pharm., 321, 371 (1988)), the bioavailability of thalidomide was poor, and posed a barrier for the administration of thalidomide extra-gastrointestinally. Also, the pharmacological research of thalidomide was affected.

Snider et al. tried to improve the solubility of the thalidomide by directly linking amino acids onto it, although such method can generate compounds with increased water-solubility. Nonetheless, even if the water-solubility of some compounds even increase to 300 mg/ml (CN1215397A), these precursors of thalidomide were not stable in the water (Bioorganic and Med. Chem. 9 (5), 1297-1291, 2001), and can only be injected immediately after the solution was prepared. Dr. Eger's group had linked the thalidomide with p-dialkylamino benzoates and got their hydrochloride salts (DE 4211812 A1). Although the water solubility of these hydrochloride salts of the thalidomide derivatives are much higher than that of thalidomide, they are easy to be de-salted and precipitated out as their correspond bases from their aqueous solutions at pH 7.5, indicating a decrease of their water solubility in condition close to physiological pH.

SUMMARY OF THE PRESENT INVENTION

A main object of the present invention is to provide novel water-soluble thalidomide derivatives for overcoming the shortcomings of the current technique. The thalidomide derivatives of the present invention are soluble in water to a certain extent within the range of physiological pH and stable in the gastric or enteric tract, thus increasing bioavailability when administered orally, and also enabling these derivatives to be administered outside the gastrointestinal tract, e.g. intravenous or intramuscular injection.

The thalidomide derivatives of the present invention is composed of compounds and various salts of relative inorganic and organic acids, with the formula as follows:

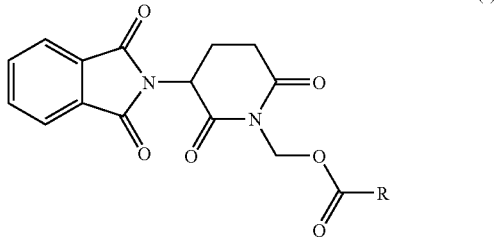

(I)

wherein: R represents $CHR^1NR^2R^3$, $CHR^1NR^4C(O)CHR^5NR^2R^3$, heterocyclic W and $CHR^5NR^4C(O)W$.

wherein: $R^1$, $R^4$ and $R^5$ independently represent H and $C_{1-4}$ alkyl group; $R^2$ and $R^3$ independently represent $C_{1-4}$ alkyl group, or $R^2$ and $R^3$ together represents 1,3-propylene, 1,4-butylene, 1,5-pentaethylene, and 1,6-hexamethylene; and W represents 4-, 5-, 6-, 7- or 8-mumbered saturated or unsaturated heterocycles, and more particularly, W represents 2-pyridyl, 3-pyridyl, 4-pyridyl, 2-imidazopyridyl, 3-imidazopyrimidinyl, 4-imidazopyridyl or heterocycles of formula (II), formula (III), formula (IV) and formula (V), wherein X represents O, S, $NR^1$, wherein $R^1$ represents H or $C_{1-4}$ alkyl group, and Y represents 1,2-ethylene, 1,3-propylene, 1,4-butylene, 1,5-pentylene, 1,6-hexatylene and hetero-atom containing bi-terminal subunits such as $CH_2OCH_2$, $CH_2SCH_2$ or $CH_2NR^6CH_2$ etc., wherein R represents H or $C_{1-4}$ alkyl group.

(II)

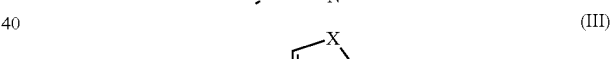

(III)

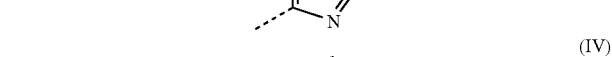

(IV)

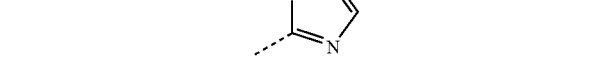

(V)

When representing $C_{1-4}$ alkyl including linear or branched chain alkyl radical, $R^1$, $R^4$, $R^5$ and $R^6$ can be substituted by OH, COOH, $C(O)NH_2$, $NHC(O)(C_{1-4}$ alkyl), $NH_2$, $NH(C_{1-4}$ alkyl), $N(C_{1-4}$ alkyl$)_2$, $NHC(O)NH_2$, $NHC(NH)NH_2$, $OC_{1-4}$ alkyl, $SC_{1-4}$ alkyl, phenyl or unsubstituted phenyl group.

When $R^2$ and $R^3$ represent $C_{1-4}$ alkyl including linear or branched alkyl radical chain, each or both of them can be substituted with OH, COOH, $C(O)NH_2$, $NHC(O)C_{1-4}$ alkyl, $NH_2$, $NHC_{1-4}$ alkyl, $N(C_{1-4}$ alkyl$)_2$, $NHC(O)NH_2$, $NHC(NH)NH_2$, $OC_{1-4}$ alkyl, $SC_{1-4}$ alkyl or other groups such as substituted or unsubstituted phenyl, etc.

$R^2$ and $R^3$ are used together to represent 1,3-propylene, 1,4-butylene, 1,5-pentylene and 1,6-hexylene, and these subunits can be substituted by OH, COOH, C(O)NH$_2$, NHC(O)C$_{1-4}$ alkyl, NH$_2$, NHC$_{1-4}$ alkyl, N(C$_{1-4}$ alkyl)$_2$, NHC(O)NH$_2$, NHC(NH)NH$_2$, OC$_{1-4}$ alkyl, SC$_{1-4}$ alkyl. But the compounds in which both R$^2$ and R$^3$ represent H are not included in the present invention.

When W is used to represent heterocycles, the heterocycles comprise 4-, 5-, 6-, 7-, and 8-mumbered saturated, unsaturated or aromatic heterocycles containing one or more heteroatom, such as N, O, S, and these heterocycles can be substituted by OH, COOH, C(O)NH$_2$, NHC(O)C$_{1-4}$ alkyl, NH$_2$, NHC$_{1-4}$ alkyl, N(C$_{1-4}$ alkyl)$_2$, NHC(O)NH$_2$, NHC(NH)NH$_2$, OC$_{1-4}$ alkyl, SC$_{1-4}$ alkyl, C$_{1-4}$ alkyl, etc.

The compounds in formula (I) which are suitable to be used as a precursor of thalidomide are those in which the R in formula (I) represents CHR$^1$NR$^2$R$^3$ where R$^1$ represents H, CH$_3$, CH(CH$_3$)$_2$, CH(CH$_3$)CH$_2$CH$_3$ or CH$_2$CH(CH$_3$)$_2$, especially where R$^1$ represents H, CH$_3$, CH(CH$_3$)$_2$, and the R$^2$ and R$^3$ independently represent CH$_3$, CH$_2$CH$_3$, as well as the R$^2$ and R$^3$ come together to represent 1,4-butylene or 1,5-pentylene, etc.

Some compounds of the formula (I) in which R represents CHR$^1$NR$^4$C(O)CHR$^5$NR$^2$R$^3$, are suitable to be used as precursors of the thalidomide. These comprise of the compounds in which R$^1$ and R$^5$ independently represent H, CH$_3$, CH(CH$_3$)$_2$, CH$_2$CH(CH$_3$)$_2$ or CH(CH$_3$)CH$_2$CH$_3$; R$^4$ represents H, CH$_3$, CH$_2$CH$_3$, CH$_2$CH$_2$CH$_3$, or CH(CH$_3$)$_2$; R$^2$ and R$^3$ independently represent CH$_3$, CH$_2$CH$_3$, CH$_2$CH$_2$CH$_3$, CH(CH$_3$)$_2$, or R$^2$ and R$^3$ come together to represent 1,4-butylene or 1,5-pentylene. Compounds, which are especially suitable to be used as the precursors of the thalidomide, include those where R$^1$ and R$^5$ independently represent H, CH$_3$ or CH(CH$_3$)$_2$; R$^4$ represents H, CH$_3$, or CH$_2$CH$_3$, R$^2$ or R$^3$ independently represent CH$_3$ or CH$_2$CH$_3$; or R$^2$ and R$^3$ come together to represent 1,4-butyl or 1,5-pentylene.

The compounds in formula (I) which are suitable to be used as a precursor of thalidomide are those in which the R in formula (I) represents W wherein W represents 2-pyridyl, 3-pyridyl, 4-pyridyl, 2-pyrimidyl, 4-pyrimidyl, 5-pyrimidyl, 2-tetrahydropyrrolyl, 2-(N-methyl) tetrahydropyrrolyl, 2-(N-ethyl) tetrahydropyrrolyl, 2-(N-propyl) tetrahydropyrrolyl, or 2-(N-isopropyl) tetrahydropyrrolyl. The compounds especially suitable to be used as the precursors of the thalidomide are those which W represents 3-pyridyl, 4-pyridyl, 2-tetrahydropyrrolyl, 2-(N-methyl) tetrahydropyrrolyl, and 2-(N-ethyl) tetrahydropyrrolyl.

The compounds in formula (I) which are suitable to be used as a precursor of thalidomide are those in which the R in formula (I) represents CHR$^5$NR$^4$C(O)W wherein R$^4$ represents H, CH$_3$, CH$_2$CH$_3$, R$^5$ represents H, CH$_3$, CH(CH$_3$)$_2$, and W represents 2-pyridyl, 3-pyridyl, 4-pyridyl, 2-pyrimidyl, 4-pyrimidyl, 5-pyrimidyl, 2-tetrahydropyrrolyl, 2-(N-methyl)tetrahydropyrrolyl, 2-(N-ethyl)tetrahydropyrrolyl, 2-(N-propyl) tetrahydropyrrolyl, or 2-(N-isopropyl)tetrahydropyrrolyl. The compounds especially suitable to be used as the precursors of the thalidomide are those which R$^4$ represents H, CH$_3$, CH$_2$CH$_3$, R$^5$ represents H, CH$_3$, CH(CH$_3$)$_2$ and W represents 3-pyridyl, 4-pyridyl, 2-tetrahydropyrrolyl, 2-(N-methyl) tetrahydropyrrolyl, and 2-(N-ethyl) tetrahydropyrrolyl.

The present invention also relates to the method of preparing thalidomide derivatives of formula (I). The steps of the method involves the reaction between the N-hydromethyl thalidomide and carboxylic acid HO$_2$CCHR$^1$NR$^2$R$^3$ or HO$_2$CCHR$^1$NR$^4$C(O)CHR$^5$NR$^2$R$^3$ or HO$_2$CW or HO$_2$CCHR$^5$NR$^4$C(O)W, with the carbodimide or carbonyldimidazole as the condensation agent, at room temperature for 2~18 hours. The mole ratio between the N-hydromethyl thalidomide and the carboxylic acid said above is 3~1:1~3, and the mole ratio between the N-hydromethyl thalidomide and the condensation agent carbodimide or carbonyldimidazole is 3~1:1~3, with or without the catalyst pyridine derivatives or other organic base, and more particularly the 4-dimethy-laminopyridine or 4-(1-pyrrolyl)pyridine. The dosage of the catalyst is between 1-20% mole of the N-hydromethyl thalidomide, and the above reaction is conducted in the organic solvents such as dichloromethane, chloroform, acetone, N,N-dimethyl formamide, dimethyl sulfoxide, ethylene glycol dimethyl ether, tetrahydrofuran, or pyridine.

The second method for the production of the precursors of thalidomide in formula (I) presented in this invention is by conducting the reaction between N-hydromethyl thalidomide and HO$_2$CCHR$^1$Br or HO$_2$CCHR$^1$NR$^4$C(O)CHBrR$^5$ under the stated conditions (above) at room temperature for 2~18 hours. Then react the products of the above reaction with 1~3 fold amount of amine or amine salt for 2~24 hours, using an organic base (such as pyridine, triethylamine etc.) or inorganic base (such as sodium carbonate, sodium bicarbonate etc.) as an acid-consuming agent, and carrying the reaction in an organic solvent such as dichloromethane, chloroform, acetone, N,N-dimethyl formamide, dimethy sulfone, ethylene glycol dimethyl ether, tetrahydrofuran or acetonitrile.

The indication of the thalidomide derivatives in formula (I) comprises, but is not limited to erythema nodosum lepresom, cutaneous erythematosus lupes persistent erythmatosus lupes, behcet's syndrome, crohn's disease, rheumatoid arthritis, abnormal myeloidosis syndrome and tumors (including, but not limited to multiple myeloma, lymphoma leukemia and hepatocarcinoma).

In addition to the thalidomide derivatives of formula (I) in this invention, some medical adjuvant material including carrier, bulk additive, dissolving-help agent, diluent, coloring material, adhesion agent etc., or other pharmaceutical active ingredient, can be used for complex formulation. The selection of the adjuvants and the dosage of the adjuvants are dependent on the pattern of the medicine administration, e.g. on whether the medicine is administered gastrointestinally, intravenously, intraperitoneally, intradermally, intramuscularly, intranasally or topically.

These and other objectives, features, and advantages of the present invention will become apparent from the following detailed description, the accompanying drawings, and the appended claims.

DETAILED DESCRIPTION OF THE PREFERRED EMBODIMENT

Abbreviation:

DCC: dicyclohexylcarbodimide; DCM: dichloromethane; TFA: trifluoroacetic acid; CDCl$_3$: deuteriochloroform; HCl: hydrochloride.

Example 1

(S)-2-(diethylaminoacetamido)-3-methyl butyric acid 2-(1-(hydroxymethyl)-2,6-dioxopiperidin-3-yl) isoindoline-1,3-dione ester hydrochloride A. Bromoacetic Acid Activated Ester Dissolve the bromoacetic acid (4.3 g, 30 mmol) and hydroxymethylsuccinimide (4.03 g, 35 mmol) in DCM (25 ml), agitating on electromagnetic stirrer over night at room temperature with one addition of the DCC (7.42 g, 36 mmol). Remove solid (cyclohexylurea) by filtration, wash the filter cake several times with DCM, then wash the pooled filtrate 3 times with saturated sodium chloride water solution (30 ml/each), dried with anhydrous magnesium sulfate, discard the desiccant, remove solvent by rotary evaporation, give a white solid (5 g, 70%).

B. (S)-2-(bromoacetamido)-3-methyl-butyric acid 2-(1-(hydroxymethyl)-2,6-dioxopiperidin-3-yl)isoindoline-1,3-dione ester Dissolving the (S)-2-amino-3-methyl butyric acid 2-(1-(hydroxymethyl)-2,6-dioxopiperidin-3-yl)isoindoline-1,3-dione ester (1.80 g, 4.7 mmol) into the DCM solution (20 ml), and adding the activation ester of the bromoacetic acid (1.04 g, 4.7 mmol), the reaction mixture is agitated on a electro-magnetic stirrer over night at room temperature. Wash the reaction solution 3 times with saturated sodium chloride water solution, dry with anhydrous magnesium sulfate, remove drying agent by filtration, remove solvent from the filtrate at vacuum give the crude product. The crude product was purified with silica gel column (mobile phase used as ethyl acetate:petroleum ether=1:1) to give a white solid (1.3 g) with a yield of 54%, $^1$H NMR (CDCl$_3$, ppm) δ 7.88-7.90 (m, 2H), 7.78-7.80 (m, 2H), 6.86 (t, 1H, J=8.4 Hz), 5.87-5.95 (m, 2H), 5.03-5.07 (m, 1H), 4.52-4.58 (m, 1H), 3.90-3.93 (m, 2H), 3.00-3.07 (m, 1H), 2.80-2.86 (m, 2H), 2.16-2.22 (m, 2H), 0.89-1.00 (m, 6H).

C. (S)-2-(diethylaminoacetylamino)-3-methyl butyric acid 2-(1-(hydroxymethyl)-2,6-dioxopiperidin-3-yl)isoindoline-1,3-dione ester Dissolve the (S)-2-(bromoacetylamino)-3-methyl butyric acid 2-(1-(hydroxymethyl)-2,6-dioxopiperidin-3-yl)isoindoline-1,3-dione ester (120 mg, 0.24 mmol) into DCM (8 ml). Slowly add the diethylamine solution (0.04 ml, 0.387 mmol) drop-by-drop into the above solution while agitating, and keep agitating at room temperature, discard the dissolvent and the residual diethylamine by spinning evaporation, the mixture solid product is purified through silica get column (mobile phase is ethyl acetate:petroleum ether=3:1), the product is 100 mg, the rate of production is 83%, $^1$H NMR (CDCl$_3$, ppm) δ 7.94 (d, 1H, J=8.4 Hz), 7.88-7.90 (m, 2H), 7.76-7.78 (m, 2H), 5.83-5.94 (m, 2H), 5.03-5.07 (m, 1H), 4.55-4.59 (m, 1H), 2.97-3.20 (m, 3H), 2.60-2.80 (m, 2H), 2.57 (q, 4H, J=6.8 Hz), 1.044 (t, 3H, J=6.8 Hz), 1.038 (t, 3H, J=6.8 Hz), 0.91-0.95 (m, 3H), 0.87 (d, 3H, J=6.8 Hz); MS: (EI) M$^+$ 500.

D. Salt-Forming Reaction

Dissolve the compound (76 mg, 0.15 mmol) from the reaction C in DCM (10 ml), add 15% HCl/methanol solution (5 mL) drop-by-drop into the abovementioned DCM solution, remove solvent in vacuum to obtain 82 mg white foam. The water solubility of this solid is >150 mg/ml, and aqueous solution stability is: $t_{1/2}$>8 hours.

Example 2

(S)-2-(dimethylaminoacetamido)-3-methyl butyric acid 2-(1-(hydroxymethyl)-2,6-dioxopiperidin-3-yl) isoindoline-1,3-dione ester hydrochloride Prepare the above compound by using the synthesis method in the example 1, but the diethylamine in example 1 is replaced by dimethylamine (yield: 53%). $^1$H NMR (CDCl$_3$, ppm) δ 7.87-7.89 (m, 2H), 7.76-7.78 (m, 2H), 7.61 (d, 1H, J=9.2 Hz), 5.92 (d, 1H, J=9.2 Hz), 5.86 (d, 1H, J=9.2 Hz), 5.03-5.07 (m, 1H), 4.55-4.58 (m, 1H), 2.97-3.06 (m, 3H), 2.82-2.87 (m, 2H), 2.31 (s, 6H), 2.16-2.22 (m, 2H), 0.95 (d, 3H, J=6.8 Hz), 0.87 (d, 3H, J=6.8 Hz); MS (EI) M$^+$ 472. The solubility of this compound in water is >150 mg/mL, and its aqueous solution stability is: $t_{1/2}$>8 hours.

Example 3

(S)-2-(1-piperidinylacetamido)-3-methyl butyric acid 2-(1-(hydroxymethyl)-2,6-dioxopiperidin-3-yl)isoindoline-1,3-dione ester hydrochloride This compound is produced by using the synthesis method of the example 1 except the diethylamine is substituted by piperidine (yield: 50%). $^1$H NMR (CDCl$_3$, ppm) δ 7.87-7.90 (m, 2H), 7.76-7.82 (m, 3H), 5.84-5.95 (m, 2H), 5.03-5.07 (m, 1H), 4.53-4.59 (m, 1H), 3.03-3.07 (m, 1H), 2.97 (s, 2H), 2.80-2.90 (m, 2H), 2.40-2.58 (m, 4H), 2.16-2.25 (m, 2H), 1.55-1.68 (m, 4H), 1.38-1.50 (m, 2H), 0.87-0.97 (m, 6H); MS (EI) M$^+$ 512. The water solubility f this compound is >150 mg/mL, and its aqueous solution stability is: $t_{1/2}$>8 hours.

Example 4

Diethylaminoacetic acid 2-(1-(hydroxymethyl)-2,6-dioxopiperidin-3-yl)isoindoline-1,3-dione ester hydrochloride

A. Bromoacretic acid 2-(1-(hydroxymethyl)-2,6-dioxopiperidin-3-yl)isoindoline-1,3-dione ester Dissolve the bromoacetic acid (138.95 mg, 1 mmol) and 2-(1-(hydroxymethyl)-2,6-dioxopiperidin-3-yl)isoindoline-1,3-dione (288 mg, 1 mmol) into the DCM (20 ml), electro-magnetic agitating at room temperature, and add the total amount of DCC (206 mg, 1 mmol) at one time, keep reacting over night. Then, remove the cyclohexylurea by filtration, wash the filter cake several times with DCM. The pooled filtrate was washed with the saturated sodium chloride aqueous solution (30 ml/each) and dried with anhydrous magnesium sulfate. After removal of the desiccant by filtration and solvent by rotary evaporation, 390 mg of white solid was obtained with a yield of 95%. $^1$H NMR (CDCl$_3$, ppm) δ 7.87-7.90 (m, 2H), 7.75-7.78 (m, 2H), 6.17 (d, 1H, J=9.6 Hz), 6.09 (d, 1H, J=9.6 Hz), 5.09-5.14 (m, 1H), 4.85 (s, 2H), 3.02-3.17 (m, 1H), 2.80-2.95 (m, 2H), 2.17-2.28 (m, 1H).

B. Diethylaminoacetic acid 2-(1-(hydroxymethyl)-2,6-dioxopiperidin-3-yl)isoindoline-1,3-dione ester Dissolve the bromoacetic acid 2-(1-(hydroxymethyl)-2,6-dioxopiperidin-3-yl)isoindoline-1,3-dione ester (409.2 mg, 1 mmol) in the DCM (10 ml). While stirring, 1M diethylamine solution in THF (1.2 ml) was added drop-by-drop at room temperature. After addition, keep stirring for 2 hours. Then remove the solvent and residual diethylamine by rotary vacuum evaporation. The crude product was purified by using silica gel column (mobile phase is: ethyl acetate:petroleum ether=2:1) to give 128 mg of white solid with a yield of 32%. $^1$H NMR (CDCl$_3$, ppm): δ 7.88-7.90 (m, 2H), 7.77-7.79 (m, 2H), 5.89 (d, 1H, J=9.2 Hz), 5.84 (d, 1H, J=9.2 Hz), 5.02-5.06

(m, 1H), 3.35 (s, 2H), 3.00-3.10 (m, 1H), 2.78-2.94 (m, 2H), 2.62-2.67 (m, 4H), 2.14-2.17 (m, 1H), 1.02-1.06 (m, 6H); MS (EI): 401 (M$^+$).

C. Salt-Formation Reaction of Compound

Dissolve diethylaminoacetic acid 2-(1-(hydroxymethyl)-2,6-dioxopiperidin-3-yl)isoindoline-1,3-dione ester (76 mg, 0.19 mmol) in DCM solution (10 ml), add 15% HCl/methanol solution (10 mL), remove the solvent by rotary evaporation to give 80 mg of white foam. Recrystallization from isopropyl ether/ethanol to give white crystal. MP: 118-122° C. Its water solubility is >150 mg/mL, and its aqueous solution stability is: $t_{1/2}$>8 hours.

Example 5

Dimethylaminoacetic acid 2-(1-(hydroxymethyl)-2,6-dioxopiperidin-3-yl)isoindoline-1,3-dione ester hydrochloride salt This compound (yield: 43%) is produced by replacing the diethylamine with dimethylamine and by using the synthesis method same as that in the example 4. $^1$H NMR (CDCl$_3$, ppm) δ 7.88-7.90 (m, 2H), 7.77-7.79 (m, 2H), 5.91 (d, 1H, J=9.8 Hz), 5.87 (d, 1H, J=9.8 Hz), 5.03-5.07 (m, 1H), 3.22 (s, 2H), 3.00-3.10 (m, 1H), 2.78-2.94 (m, 2H), 2.36 (s, 6H), 2.15-2.20 (m, 1H); MS (EI) M$^+$ 373. The solubility of this compound in water is >150 mg/mL, and its aqueous solution stability is: $t_{1/2}$>4 hours.

Example 6

(S)-2-diethylamino-3-methyl butyric acid 2-(1-(hydroxymethyl)-2,6-dioxopiperidin-3-yl)isoindoline-1,3-dione ester Dissolve the (S)-2-amino-3-methyl butyric acid 2-(1-(hydroxymethyl)-2,6-dioxopiperidin-3-yl)isoindoline-1,3-dione ester (90 mg, 0.23 mmol) in acetonitrile (8 ml), then add ethyl iodide (74 mg, 0.48 mmol) into the solution, agitate the resulted mixture over night at 80° C. Remove the solvent by rotary evaporation to give a crude product, purify the crude product by using silica gel column (mobile phase is ethyl acetate:petroleum ether=1:1) to give a white solid (30 mg, 31%). $^1$H NMR (CDCl$_3$, ppm): δ 7.88-7.90 (m, 2H), 7.77-7.79 (m, 2H), 5.89 (d, 1H, J=9.2 Hz), 5.84 (d, 1H, J=9.2 Hz), 5.02-5.06 (m, 1H), 3.45 (m, 1H), 3.00-3.10 (m, 1H), 2.78-2.94 (m, 2H), 2.62-2.67 (m, 4H), 2.14-2.17 (m, 2H), 1.02-1.06 (m, 6H), 0.87-0.97 (m, 6H); MS (EI) 443 (M$^+$).

Example 7

(S)-Proline 2-(1-(hydroxymethyl)-2,6-dioxopiperidin-3-yl)isoindoline-1,3-dione ester TFA salt Dissolve the (S)-tert-butoxycarbonyl proline (374 mg, 1.74 mmol) and 2-(1-(hydroxymethyl)-2,6-dioxopiperidin-3-yl)isoindoline-1,3-dione (500 mg, 1.7 mmol) in the DCM (30 ml), electromagnetic stirring at room temperature with one addition of DCC (350.2 mg, 1.7 mmol) and DMAP (p-dimethylaminopyridine)(25 mg), keep reacting over night. Remove the cyclohexylurea by filtration, and wash the filter cake several times with DCM. The pooled filtrate was washed with water and saturated NaCl aqueous solution, dried with anhydrous magnesium sulfate. Remove desiccant by filtration and solvent by rotary evaporation to give a crude product. Purify the crude product using column (solid phase is silica, mobile phase is chloroform:acetone=9:2) to give (S)-tert-butoxycarbonyl proline 2-(1-(hydroxymethyl)-2,6-dioxopiperidin-3-yl)isoindoline-1,3-dione ester as a white solid (658 mg, 80%).

Dissolve (S)-tert-butoxycarbonyl proline 2-(1-(hydroxymethyl)-2,6-dioxopiperidin-3-yl)isoindoline-1,3-dione ester (658 mg, 1.35 mmol) in the 25% TFA/DCM (20 mL). After electromagnetic stirring for 4 hours at room temperature, remove the DCM and most of TFA by rotary evaporation, dry in vacuum to give (S)-Proline 2-(1-(hydroxymethyl)-2,6-dioxopiperidin-3-yl)isoindoline-1,3-dione ester TFA salt as a foam (500 mg, 100%). $^1$H NMR (CDCl$_3$, ppm): δ 9.80 (brs, 1H), 9.0 (brs, 1H), 7.90-8.00 (m, 4H), 5.75-5.95 (m, 2H), 5.35-5.42 (m, 1H), 4.38-4.48 (m, 1H), 3.15-3.30 (m, 2H), 3.04-3.15 (m, 1H), 2.80-2.92 (m, 1H), 2.50-2.70 (m, 1H), 2.12-2.28 (m, 2H), 1.80-2.00 (m, 3H); MS (EI): 385 (M$^+$).

Example 8

(S)-2-(isonicotinamido)-3-methy butyric acid 2-(1-(hydroxymethyl)-2,6-dioxopiperidin-3-yl)isoindoline-1,3-dione ester Dissolve (S)-2-amino-3-methyl butyric acid 2-(1-(hydroxymethyl)-2,6-dioxopiperidin-3-yl)isoindoline-1,3-dione ester (200 mg, 0.5 mmol) and isonicotonic acid N-hydroxymethylsuccinimide ester (120 mg, 0.54 mmol) in DCM (20 ml). Keep stirring at room temperature after triethylamine (1 ml) added at one time over night. Then, transfer the reaction solution into DCM (30 ml), wash this solution three time with saturated sodium hydrogen carbonate aqueous solution (30 ml/each time), then washed with saturated sodium chloride aqueous solution (30 ml), dry with the desiccant anhydrous magnesium sulfate. Remove the desiccant by filtration and remove the solvent by rotary evaporation to give the crude product which give a white solid (239 mg, 97%) after purification through silica gel column (mobile phase is: chloroform:acetone=5:2). $^1$HNMR (CDCl$_3$, ppm): δ 9.04 (d, 1H, J=11.2 Hz), 8.72 (s, 1H), 8.13 (d, 1H, J=8.0 Hz), 7.87-7.90 (m, 2H), 7.76-7.78 (m, 2H), 7.41 (dd, 1H, J=8.0, 11.2 Hz), 6.73 (d, 1H, J=9.6 Hz), 5.86-5.98 (m, 2H), 5.05-5.08 (m, 1H), 3.00-3.15 (m, 1H), 2.80-2.95 (m, 2H), 2.12-2.28 (m, 1H), 2.10-2.20 (m, 2H), 0.97-1.05 (m, 3H), 0.85-0.88 (m, 3H).

Example 9

(S)-2-(isonicotinamido)propionic acid 2-(1-(hydroxymethyl)-2,6-dioxopiperidin-3-yl)isoindoline-1,3-dione ester Dissolve the (S)-2-(isonicotinamido)propionic acid (582.5 mg, 3 mmol) and 2-(1-(hydroxymethyl)-2,6-dioxopiperidin-3-yl)isoindoline-1,3-dione (864 mg, 3 mmol) in DCM (25 ml), toward where add DCC (618 mg, 3 mmol) at one time during electromagnetic stirring at room temperature, keep the agitation over night. Remove the cyclohexylurea by filtration, wash the filter-cake several times with DCM. The pooled filtrate was washed three times with saturated sodium chloride aqueous solution (30 ml/time), dried with the desiccant anhydrous magnesium sulfate. After removal of the solvent by rotary evaporation to give crude product, which give 975 mg white solid (yield 70%) after purification using silica gel column (mobile phase: dichloromethane:acetone=5:2). $^1$H NMR (CDCl$_3$, ppm): δ 9.14 (s, 1H), 8.75 (d, 1H, J=4.8 Hz), 8.23 (d, 1H, J=10.4 Hz), 7.87-7.90 (m, 2H), 7.76-7.78 (m, 2H), 7.47 (dd, 1H, J=4.8, 10.4 Hz), 7.15 (d, 1H, J=9.6 Hz), 5.90-6.05 (m, 2H), 5.07-5.12 (m, 1H), 4.78-4.92 (m, 1H), 3.00-3.15 (m, 1H), 2.75-2.95 (m, 2H), 2.12-2.20 (m, 1H), 1.50-1.56 (m, 3H).

Example 10

Isonicotinic acid 2-(1-(hydroxymethyl)-2,6-dioxopiperidin-3-yl)isoindoline-1,3-dione ester Isonicotinic acid 2-(1-(hydroxymethyl)-2,6-dioxopiperidin-3-yl)isoindoline-1,3-dione ester is produced using the synthesis method in example 9 and using the isonicontinic acid to substitute the (S)-2-(isonicotinamiino) propionic acid (yield 70%). $^1$H NMR (CDCl$_3$, ppm): δ 9.2 (s, 1H), 8.78 (d, 1H, J=4.0 Hz), 8.29 (d, 1H, J=8.0 Hz), 7.87-7.90 (m, 2H), 7.75-7.78 (m, 2H), 7.41 (dd, 1H, J=4.0, 8.0 Hz), 6.17 (d, 1H, J=9.6 Hz), 6.09 (d, 1H, J=9.6 Hz), 5.09-5.14 (m, 1H), 3.02-3.17 (m, 1H), 2.80-2.95 (m, 2H), 2.17-2.28 (m, 1H).

Example 11

(S)-1-Ethylproline 2-(1-(hydroxymethyl)-2,6-dioxopiperidin-3-yl)isoindoline-1,3-dione ester (S)-1-Ethylproline 2-(1-(hydroxymethyl)-2,6-dioxopiperidin-3-yl)isoindoline-1,3-dione ester is prepared using the synthesis method of the example 6 with the (S)-2-amino-3-methyl butyric acid 2-(1-(hydroxymethyl)-2,6-dioxopiperidin-3-yl)isoindoline-1,3-dione ester substituted by (S)-proline 2-(1-(hydroxymethyl)-2,6-dioxopiperidin-3-yl) isoindoline-1,3-dione ester (yield 73%). $^1$H NMR (CDCl$_3$, ppm): δ 7.86-7.95 (m, 4H), 5.75-5.95 (m, 2H), 5.35-5.42 (m, 1H), 4.12-4.18 (m, 1H), 3.43 (q, 2H, J=8.4 Hz), 2.92-3.15 (m, 3H), 2.80-2.92 (m, 1H), 2.50-2.70 (m, 1H), 2.00-2.18 (m, 2H), 1.75-1.90 (m, 3H), 1.09 (t, 3H, J=8.4 Hz); MS (EI): 413 (M$^+$).

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure form such principles. Therefore, this invention includes all modifications encompassed within the spirit and scope of the following claims.

What is claimed is:

1. A compound of formula (I)

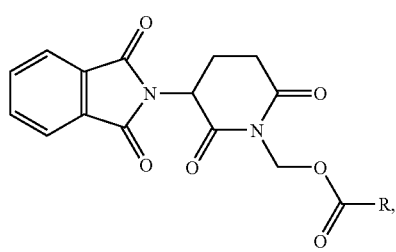

(I)

or a pharmaceutically acceptable salt thereof, wherein:
R represents, a heterocycle W or CHR$^5$NR$^4$C(O)W,
R$^4$ and R$^5$ independently represent H or C$_{1-4}$ alkyl,
W represents 2-pyridyl, 3-pyridyl, 4-pyridyl, 2-pyrimidyl, 3-pyrimidyl, 4-pyrimidyl or the heterocycles in formula (II), formula (III), or formula (IV)

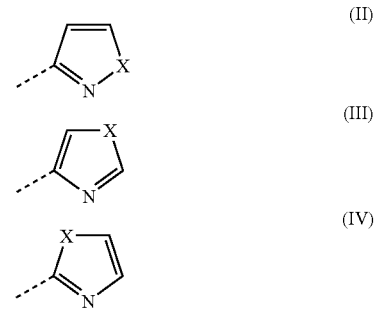

X represents O, S, NR$^1$; and
R$^1$ represents H or C$_{1-4}$ alkyl.

2. The compound of claim 1, wherein
W represents 2-pyridyl, 3-pyridyl, 4-pyridyl or the heterocycles in the formula (II), formula (III), or formula (IV),
X represents O, S or NR$^1$, and
R$^1$ represents H, CH$_3$, CH$_2$CH$_3$, CH$_2$CH$_2$CH$_3$ or CH(CH$_3$)$_2$.

3. The compound of claim 1, wherein
R represents CHR$^5$NR$^4$C(O)W;
R$^4$ and R$^5$ independently represent H, CH$_3$, CH$_2$CH$_3$, CH$_2$CH$_2$CH$_3$, or CH(CH$_3$)$_2$;
W represents 2-pyridyl, 3-pyridyl, 4-pyridyl, 2-pyrimidyl, 3-pyrimidyl, 4-pyrimidyl, or the heterocycle of formula (II), (III) or (IV);

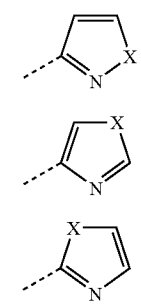

X represents O, S, NR$^1$; and R$^1$ represents H, CH$_3$, CH$_2$CH$_3$, CH$_2$CH$_2$CH$_3$, or CH(CH$_3$)$_2$.

4. A method of preparing the compound of claim 1, said method comprising: contacting N-(hydroxymethyl)thalidomide with RCOOH at room temperature and in the presence of a carbodiimide or a carbonyldiimidazole, wherein R is as defined in claim 1.

5. A pharmaceutical composition comprising a compound of claim 1 and a pharmaceutically acceptable excipient.

* * * * *